(12) United States Patent
Roberts (10) Patent No.: US 7,872,781 B2
(45) Date of Patent: Jan. 18, 2011

(54) ARTIFACT SCANNING WITH INFRARED RADIATION GENERATED WITHIN A COLD CATHODE LAMP

(75) Inventor: David Troy Roberts, Loveland, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 977 days.

(21) Appl. No.: 11/724,845

(22) Filed: Mar. 16, 2007

(65) Prior Publication Data
US 2008/0224043 A1 Sep. 18, 2008

(51) Int. Cl.
H04N 1/04 (2006.01)

(52) U.S. Cl. .................. 358/474; 358/487; 358/501; 358/509; 358/475; 382/294; 382/293; 382/318; 250/338.1

(58) Field of Classification Search .......... 358/474, 358/487, 486, 497, 488, 482, 483, 496, 509, 358/475; 250/338.1; 382/294, 293, 318
See application file for complete search history.

(56) References Cited

U.S. PATENT DOCUMENTS

| | | | |
|---|---|---|---|
| 4,000,503 A | 12/1976 | Matare | |
| 5,266,805 A * | 11/1993 | Edgar | 250/330 |
| 5,765,701 A * | 6/1998 | Gearin et al. | 211/85.8 |
| 5,781,311 A * | 7/1998 | Inoue et al. | 358/475 |
| 5,898,171 A | 4/1999 | McConica et al. | |
| 6,078,051 A * | 6/2000 | Banton et al. | 250/341.1 |
| 6,252,684 B1 * | 6/2001 | Lin | 358/498 |
| 6,327,056 B1 * | 12/2001 | Tsai et al. | 358/474 |
| 6,380,539 B1 | 4/2002 | Edgar | |
| 6,752,684 B1 * | 6/2004 | Lee | 446/456 |
| 6,765,701 B2 | 7/2004 | Yang et al. | |
| 6,768,565 B1 * | 7/2004 | Perregaux et al. | 358/505 |
| 6,796,502 B2 | 9/2004 | Nogami et al. | |
| 6,891,645 B1 | 5/2005 | Nakamura | |
| 7,006,705 B2 | 2/2006 | Takayama et al. | |
| 7,088,477 B2 | 8/2006 | Koshimizu et al. | |
| 7,110,150 B2 | 9/2006 | Tecu et al. | |
| 7,113,619 B1 * | 9/2006 | Matama | 382/112 |
| 7,257,274 B2 * | 8/2007 | Brothers et al. | 382/298 |
| 7,541,588 B2 * | 6/2009 | Tabirian et al. | 250/341.1 |
| 2003/0112481 A1 | 6/2003 | Wang et al. | |
| 2005/0157353 A1 * | 7/2005 | Nishinohara et al. | 358/474 |
| 2005/0275908 A1 * | 12/2005 | Nogami et al. | 358/497 |
| 2006/0238128 A1 * | 10/2006 | Chen | 313/635 |
| 2006/0268367 A1 * | 11/2006 | Hayashide | 358/474 |
| 2009/0161191 A1 * | 6/2009 | Powell | 359/207.7 |

FOREIGN PATENT DOCUMENTS

JP 07021904 A 1/1995

* cited by examiner

Primary Examiner—Negussie Worku (57) ABSTRACT

Visible and infrared radiation is generated from phosphors within a cold cathode lamp. At least partially transparent media is irradiated with the visible and infrared radiation from the cold cathode lamp. Infrared radiation that passes through the at least partially transparent media is sensed, and an artifact signal is generated from the sensed infrared radiation. The artifact signal corresponds to one or more unwanted artifacts on the at least partially transparent media.

25 Claims, 9 Drawing Sheets

ARTIFACT SCANNING WITH INFRARED RADIATION GENERATED WITHIN A COLD CATHODE LAMP

BACKGROUND

Some image-capturing devices, such as scanners, are configured to scan opaque media and at least partially transparent media, such as transparencies, photo-negatives, slides, etc. Typically, the transparent media is scanned with visible light from a visible-light source, such as a cold cathode lamp. The visible light passes through the transparent media and is projected onto a sensor, such as a charge-coupled device (CCD) image sensor, that converts the visible light into an image signal that contains image data corresponding to images on the transparent media. Data corresponding to unwanted artifacts, such as scratches, dust, and/or other defects, that may be on the transparent media are also contained in the image signal and can degrade the images produced from the image signal. Therefore, a separate scan of the transparent media is typically performed using infrared radiation from a separate infrared radiation source, such as a bank of infrared light-emitting diodes, to produce an artifact signal that contains data corresponding to the artifacts. The artifact signal can be used in conjunction with the image signal to remove the artifacts from the image signal. However, a separate infrared radiation source, especially a bank of infrared light-emitting diodes, can be expensive and can significantly impact the cost of the scanner.

DETAILED DESCRIPTION

In the following detailed description of the present embodiments, reference is made to the accompanying drawings that form a part hereof, and in which are shown by way of illustration specific embodiments that may be practiced. These embodiments are described in sufficient detail to enable those skilled in the art to practice disclosed subject matter, and it is to be understood that other embodiments may be utilized and that process, electrical or mechanical changes may be made without departing from the scope of the claimed subject matter. The following detailed description is, therefore, not to be taken in a limiting sense, and the scope of the claimed subject matter is defined only by the appended claims and equivalents thereof.

Figure 1:
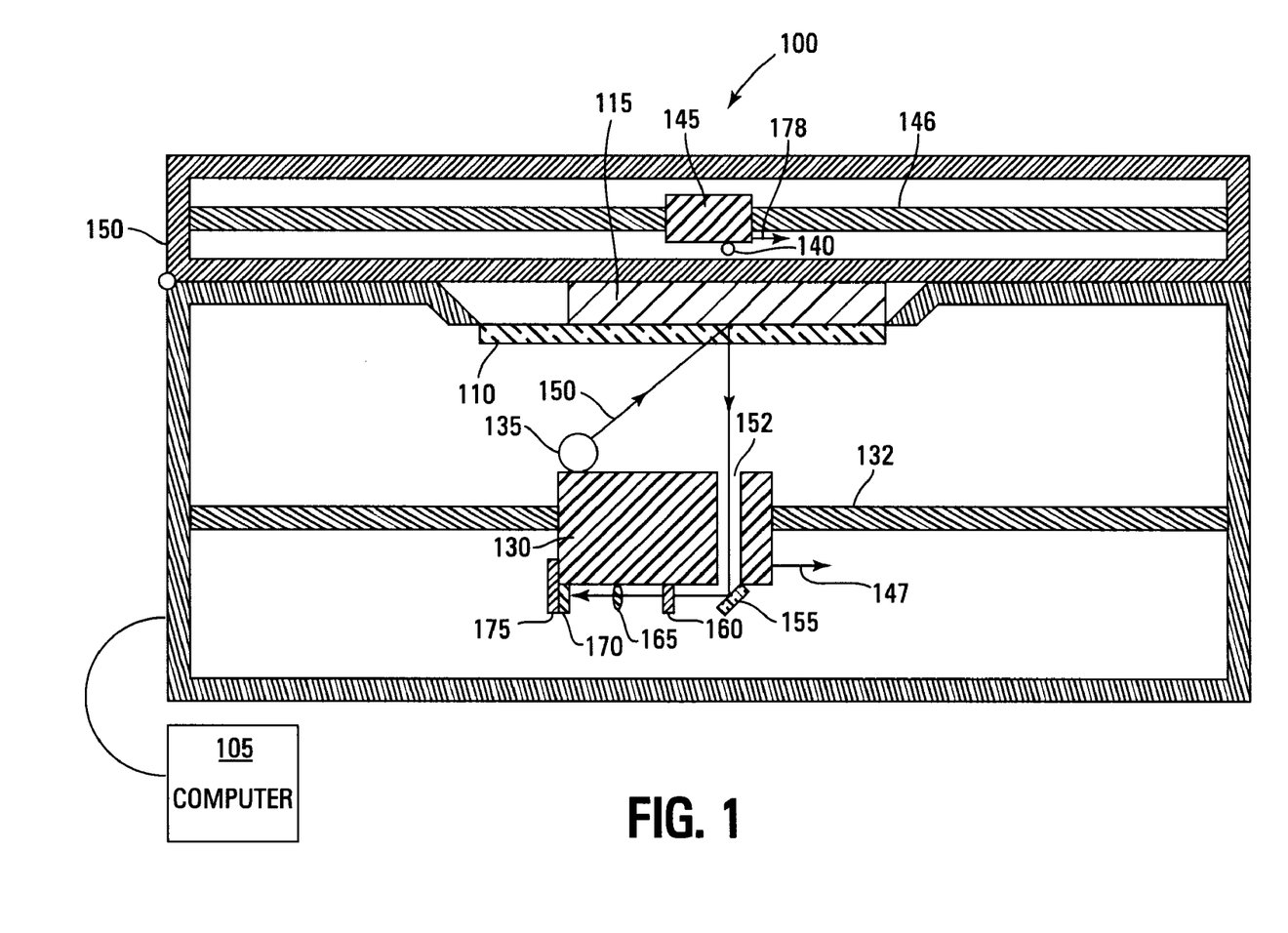
FIG. 1 is a cross-sectional side view of an embodiment of a scanner operating in an opaque scanning mode, according to an embodiment of the disclosure.
Figure 2:
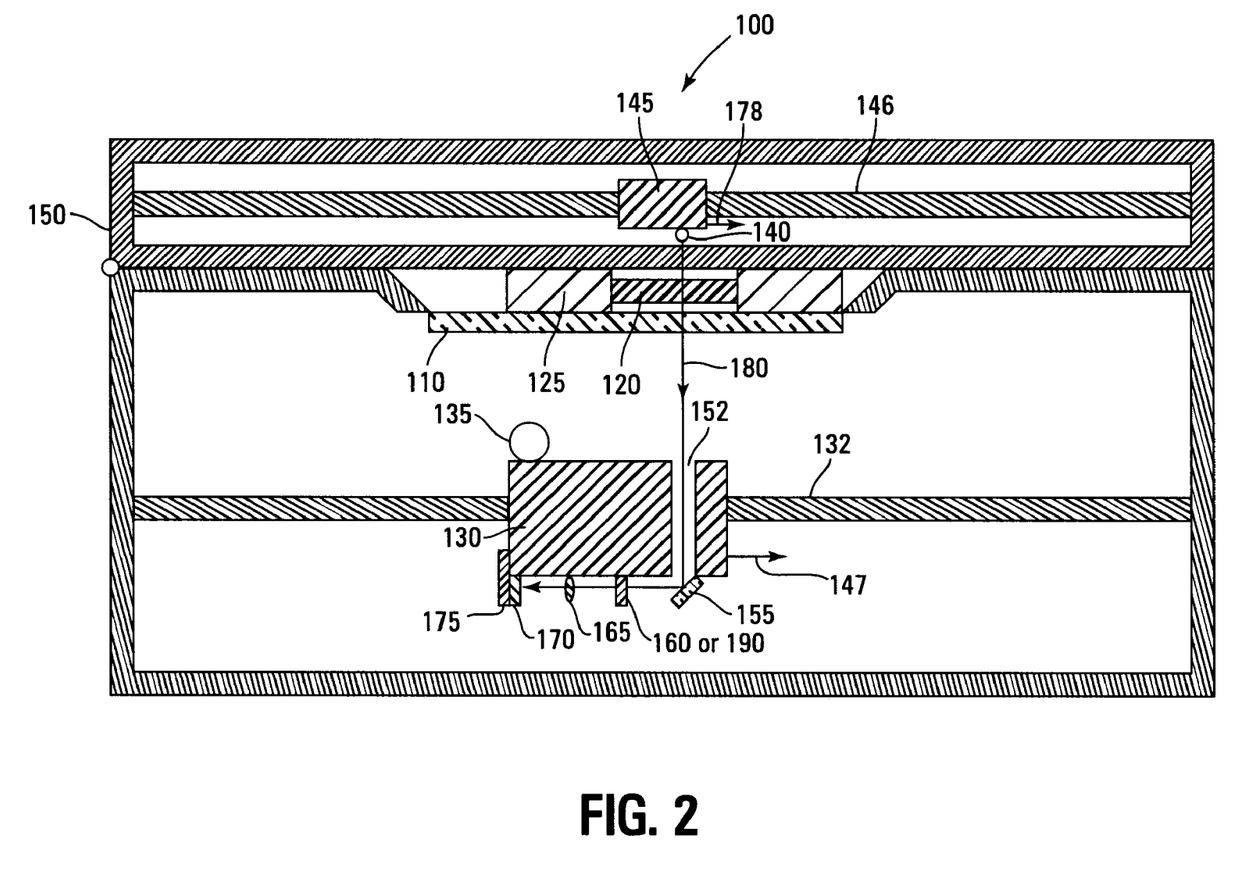
FIG. 2 is a cross-sectional side view of an embodiment of a scanner operating in a transparent scanning mode, according to another embodiment of the disclosure.

FIGS. 1 and 2 are cross-sectional side views of a scanner 100 respectively operating in an opaque scanning mode and a transparent scanning mode, according to an embodiment. For one embodiment, scanner 100 may be an integral portion of a copier, facsimile machine, an all-in-one, etc. Scanner 100 has a platen 110, e.g., of clear glass or plastic, that is substantially transparent to visible light and to at least a portion of the infrared spectrum. Platen 110 receives substantially opaque media 115, such as paper, for scanning in the opaque scanning mode and at least partially transparent media, or media substantially transparent to visible light and infrared radiation (hereinafter referred to as transparent media), such as transparencies, photo-negatives, slides, etc., for scanning in the transparent scanning mode. For another embodiment, the transparent media, such as transparent media 120, may be disposed in a template 125, as shown in FIG. 2. For another embodiment, scanner 100 may be electronically coupled to an external computer 105, as shown in FIG. 1.

Scanner 100 includes a movable carriage 130 that underlies platen 110, and thus opaque media 115. For one embodiment, carriage 130 may ride on a rail 132, as shown in FIGS. 1 and 2, or within slots that provide a track (not shown). A radiation source, such as a light source 135, e.g., a cold cathode lamp, a cold cathode fluorescent lamp, or the like, is connected to carriage 130 for movement therewith. Note that light source 135 also underlies platen 110 and thus opaque media 115.

For one embodiment, scanner 100 may include a cold cathode lamp 140, e.g., a cold cathode fluorescent lamp, connected to a movable carriage 145 for movement therewith. Carriage 145 may ride on a rail 146, as shown in FIGS. 1 and 2, or within slots that provide a track (not shown). Carriage 145 and cold cathode lamp 140 overlie platen 110 and the transparent media. For one embodiment, carriage 145, with cold cathode lamp 140 connected thereto, may disposed in a cover 150, as shown in FIGS. 1 and 2, that may be pivotally attached to scanner 100 so that cover 150 can be made to selectively cover (or overlie) platen 110. For another embodiment, carriage 145, with cold cathode lamp 140 connected thereto, may disposed in an adaptor (often called a transparent media adapter) that may be positioned on platen 110 for scanning in the transparent scanning mode and removed when scanner 100 scans in the opaque scanning mode.

For one embodiment, cold cathode lamp 140 contains visible-light (e.g., red, green, and blue light) producing phosphores and infrared-producing phosphors that when electrically excited respectively produce visible and infrared radiation having about the same intensities. That is, visible light is generated from the visible-light producing phosphores and infrared radiation is generated from the infrared-producing phosphors concurrently. For another embodiment, the infrared-producing phosphors are added to existing phosphors, e.g., for producing visible light, contained within a conventional cold cathode lamp to configure that lamp to emit infrared radiation at an intensity of about the same level as that lamp emits visible light.

Figure 3:
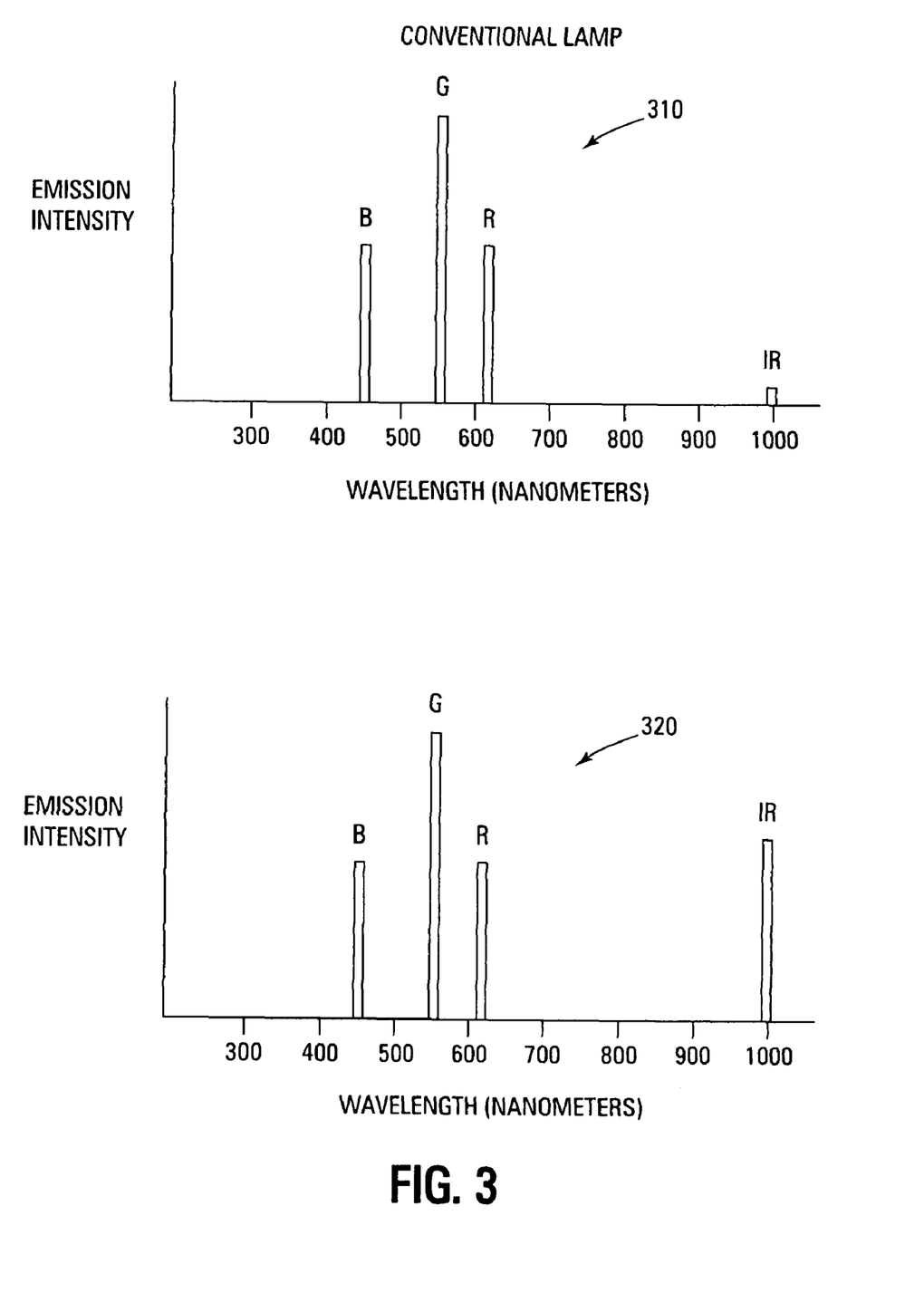
FIG. 3 compares an example of an emission intensity spectrum for a conventional cold cathode lamp to an example of an emission intensity spectrum for an embodiment of a cold cathode lamp, according to an embodiment of the disclosure.

FIG. 3 compares an example of an emission intensity spectrum 310 for a conventional cold cathode lamp to an example of an emission intensity spectrum 320 for an embodiment of cold cathode lamp 140 that contains infrared-producing phosphores for increasing the infrared emission. Emission intensity spectrum 310 for the conventional cold cathode lamp shows that the conventional cold cathode lamp may emit infrared radiation at a relatively low intensity. However, emission intensity spectrum 320 for the embodiment of cold cathode lamp 140 of FIG. 3 shows that the intensity of the infrared emission is at least about the same as the emission intensities for the red and blue light. For one embodiment, the phosphores added to cold cathode lamp 140 may act to increase the infrared-emission intensity by about a factor of ten over the infrared-emission intensity of the conventional cold cathode lamp.

Carriage 130 moves in the direction of arrow 147, relative to opaque media 115, while scanning opaque media 115, as shown in FIG. 1. When scanning is completed, carriage 130 is moved in the direction opposite to arrow 147 to an initial position from where another scan may be initiated.

When scanning opaque media 115 in the opaque scanning mode, light 150, e.g., visible light, from light source 135 is directed through platen 110 and onto a downward facing surface of opaque media 115, as shown in FIG. 1. For one embodiment, the downward facing surface of opaque media 115 may reflect light 150, e.g., downward, through an opening 152 in an upper surface of carriage 130, and extending through carriage 130, and onto a mirror 155 that may be attached to the bottom of carriage 130, as shown in FIG. 1. Mirror 155 reflects the light through a filter 160 that for one embodiment may be attached to the bottom of carriage 130, as shown in FIG. 1. Note that for another embodiment, mirror 155 may turn the light by about 90 degrees from the vertical before the light arrives at filter 160, as shown in FIG. 1. For one embodiment, filter 160 can filter out or block the transmission of infrared radiation.

After passing through filter 160, the light is directed through a lens 165 that for one embodiment may be attached to the bottom of carriage 130, as shown in FIG. 1. For one embodiment, filter 160 may be optional during the opaque scanning mode and may be actuated out of the light path during the opaque scanning mode so that the light is directed directly from mirror 155 to lens 165. Lens 165 directs the light onto a sensor 170, such as a photosensitive device, e.g., an array of charge-coupled devices (or CCDs), that may be electrically connected to a circuit board 175 that may be attached to carriage 130, as shown in FIG. 1. Sensor 170 converts light received thereat into one or more electronic signals that correspond to one or more images on opaque media 115. For one embodiment, the electronic signals are sent to computer 105 (FIG. 1) for processing.

When scanning the transparent media, such as transparent media 120 disposed in template 125 (FIG. 2), during the transparent scanning mode, carriage 130 moves in the direction of arrow 147, relative to the transparent media, as shown in FIG. 2. As carriage 130 moves, carriage 145 moves concurrently with carriage 130 in the direction of arrow 178, relative to the transparent media, so that cold cathode lamp 140 remains aligned with opening 152, as shown in FIG. 2 for one embodiment.

Figure 4:
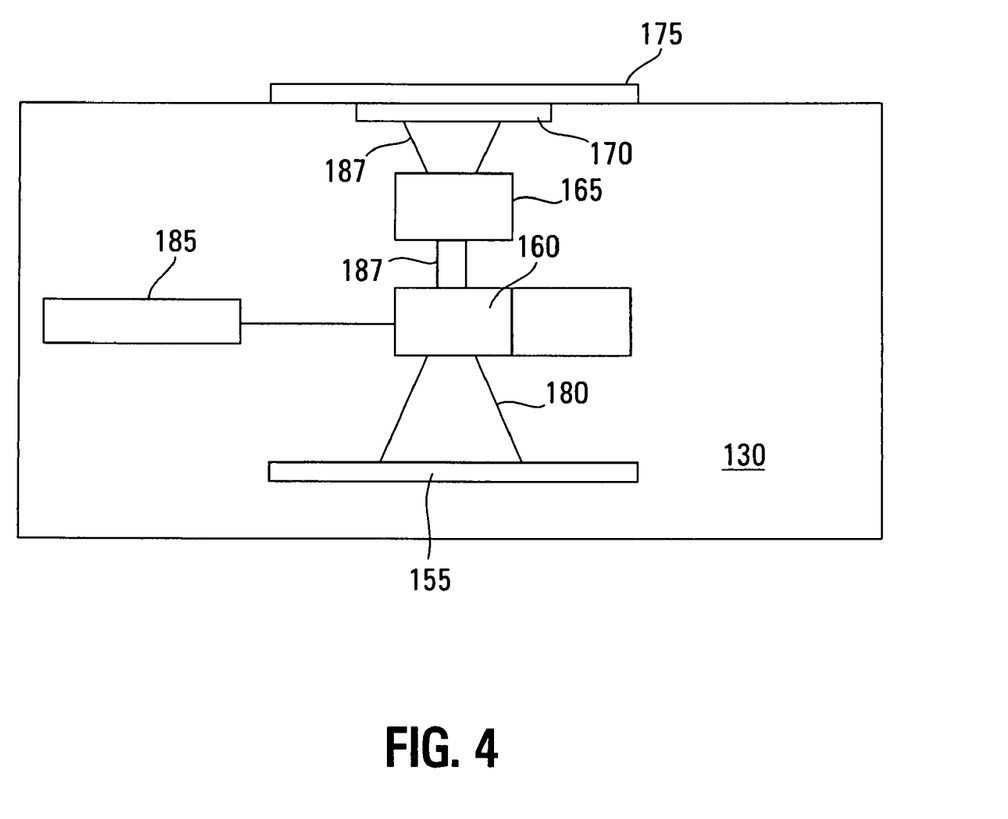
FIG. 4 is a bottom view of an embodiment of a scanner carriage configured to perform a visible scan, according to another embodiment of the disclosure.

Scanning the transparent media in the transparent scanning mode involves a visible or visible-light scan to capture one or more images on the transparent media and an infrared-radiation scan to capture unwanted artifacts, such as dust or scratches, on the transparent media. FIG. 4 is a bottom view of carriage 130 configured for performing the visible-light scan of the transparent scanning mode of scanner 100. For a visible-light scan, filter 160 is actuated between mirror 155 and lens 165 and into the path for radiation 180, emitted from cold cathode lamp 140, using an actuator 185, such as a solenoid. Note that as described above, filter 160 filters out or blocks infrared radiation.

During the visible-light scan, radiation 180, e.g., having an emission intensity spectrum similar to emission intensity spectrum 320 of FIG. 3, irradiates the transparent media, such as transparent media 120 disposed in template 125, disposed on platen 110, for example. Radiation 180 that passes through the transparent media is directed into the opening 152 in carriage 130, as shown in FIG. 2. Radiation 180 passes through opening 152 and onto mirror 155. Mirror 155 reflects radiation 180 through filter 160, as shown in FIGS. 2 and 4. Filter 160 filters out or blocks the infrared component of radiation 180 and passes visible light components 187 to lens 165, which focuses visible light components 187 onto sensor 170. Sensor 170 converts the visible light into an image signal that contains image data corresponding to one or more images on the transparent media and any unwanted artifacts that may be present on the transparent media. The image signal may be subsequently processed by firmware of scanner 100 of by software of computer 105.

Figure 5:
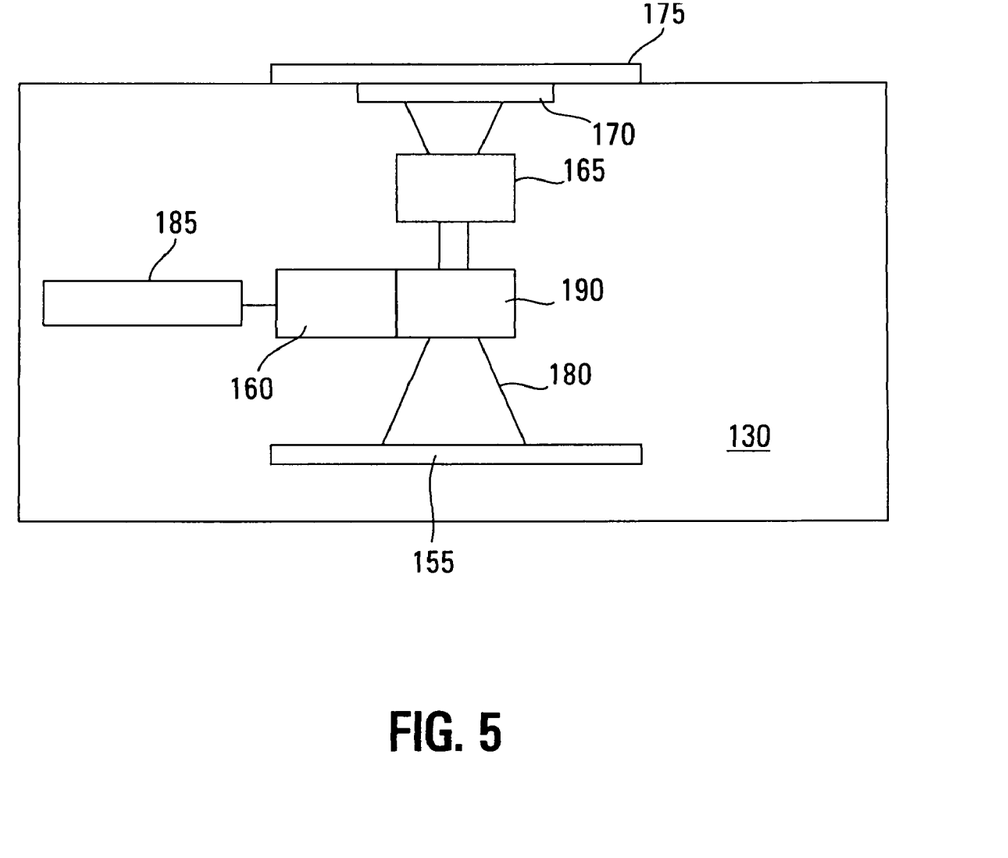
FIG. 5 is a bottom view of an embodiment of a scanner carriage configured to perform an infrared scan, according to another embodiment of the disclosure.

FIG. 5 is a bottom view of carriage 130 configured for performing the infrared-radiation scan of the transparent scanning mode of scanner 100. For an infrared-radiation scan, a focus shifter 190 is actuated between mirror 155 and lens 165 and into the path for radiation 180 using actuator 185, as shown in FIG. 5, so that mirror 155 reflects radiation 180 that passes through the irradiated transparent media through focus shifter 190. Because the infrared component has a substantially different wavelength than the visible light, it is out focus when it arrives at sensor 170 after passing through lens 165 without using focus shifter 190 in that lens 165 is configured to focus the visible light onto sensor 170. Therefore, focus shifter 190 shifts the focal point of the infrared component so that the infrared component is focused onto sensor 170 after passing through lens 165. Focus shifter 190 also shifts the focal point of the visible light components of radiation 180 so that they are out of focus when they arrive at sensor 170, thereby effectively preventing the visible light components from being sensed by sensor 170. That is, focus shifter 190 defocuses the visible light components from sensor 170.

Sensor 170 converts the infrared component into an artifact signal containing data corresponding to one or more unwanted artifacts on the transparent media. Note that the infrared radiation passes through the transparent media where there are no artifacts and is sensed by sensor 170. However, the infrared radiation is reflected by the artifacts. The radiation reflected by the artifacts does not reach sensor 170, so the sensed radiation has voids where the artifacts occur, enabling sensor to produce the artifact signal containing data corresponding to unwanted artifacts on the transparent media. The artifact signal may be subsequently processed by firmware of scanner 100 or by software of computer 105. For one embodiment, the artifact data and the image data may be compared, e.g., using firmware of scanner 100 or software of computer 105, for identifying the artifacts in the image data and removing the artifacts from the image data, as is known in the art.

For some embodiments, filter 160 and focus shifter 190 may be disposed on a rotatable wheel driven by a motor. In operation, the motor rotates the wheel to position filter 160 or focus shifter 190 in the path for radiation 180.

For other embodiments, filter 160 and focus shifter 190 constitute a selector for selectively directing the visible or infrared radiation from cold cathode lamp 140 that passes through the transparent media to sensor 175 via lens 165.

Therefore, in the transparent scanning mode, the transparency is irradiated or scanned concurrently with visible and infrared radiation, and the selector selectively directs the visible radiation to sensor 175 during the visible scan or selectively directs the infrared radiation to sensor 175 during the infrared scan.

Figure 6:
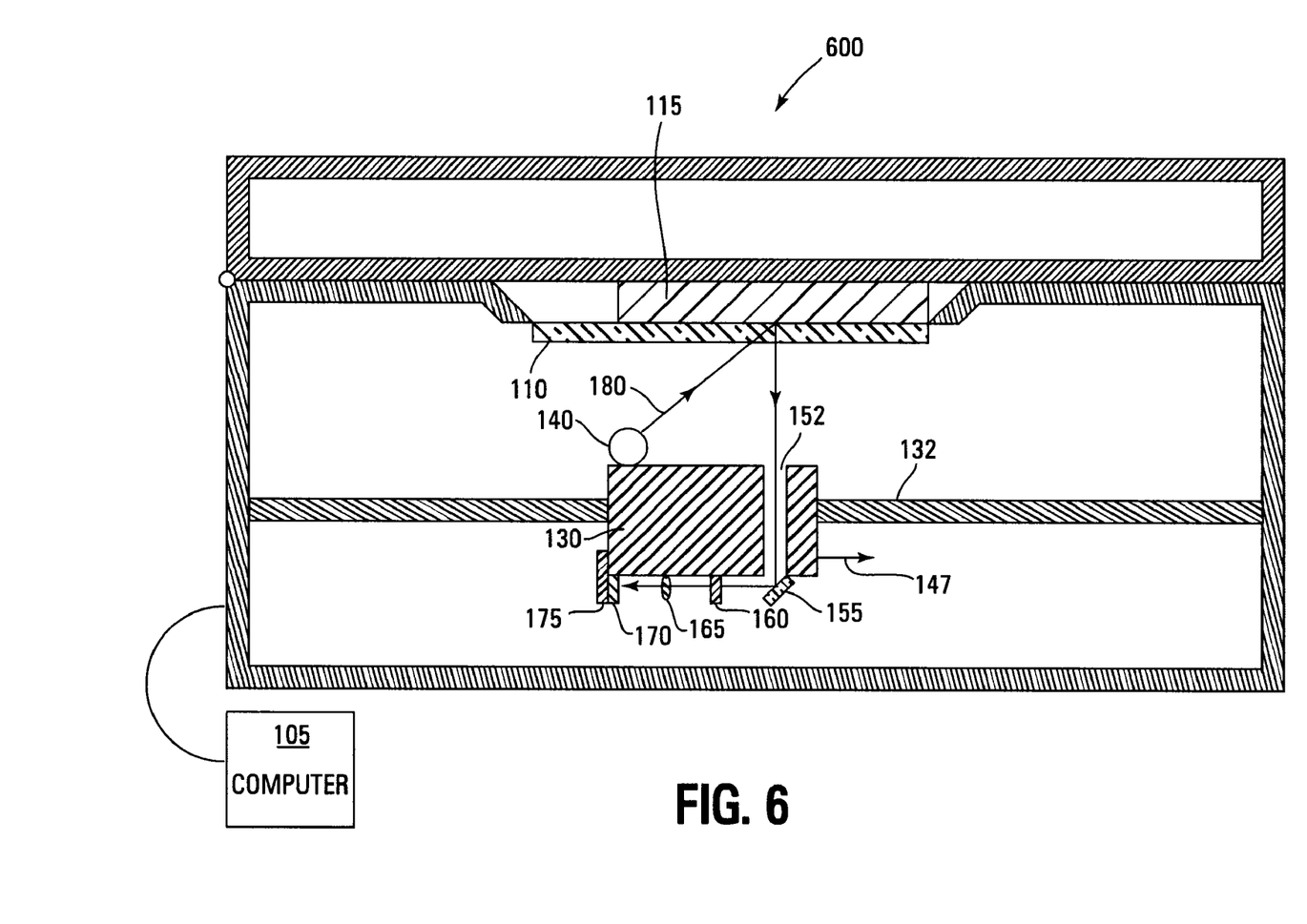
FIG. 6 is a cross-sectional side view of another embodiment of a scanner operating in an opaque scanning mode, according to another embodiment of the disclosure.
Figure 7:
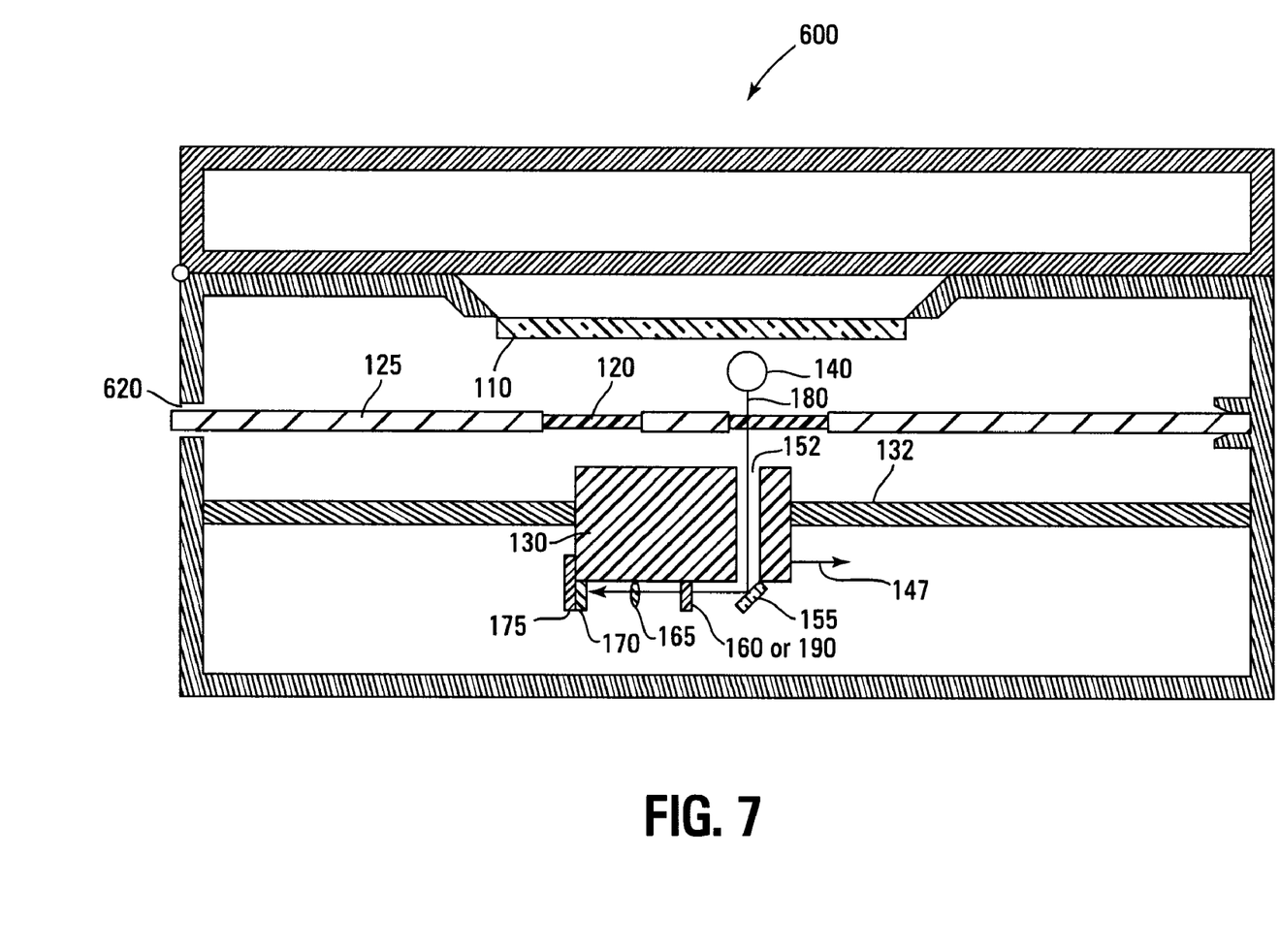
FIG. 7 is a cross-sectional side view of another embodiment of a scanner operating in a transparent scanning mode, according to another embodiment of the disclosure.

FIGS. 6 and 7 are cross-sectional side views of a scanner 600 respectively operating in an opaque scanning mode and a transparent scanning mode, according to another embodiment. Common reference numbers are used to denote substantially similar or common elements of FIGS. 1, 2, 6, and 7. For one embodiment, scanner 600 may be an integral portion of a copier, facsimile machine, an all-in-one, etc.

For one embodiment, cold cathode lamp 140 is connected to movable carriage 130 for movement therewith. In the opaque scanning mode of FIG. 6, radiation 180, emitted from cold cathode lamp 140, is directed through platen 110 and onto a downward facing surface of opaque media 115, as shown in FIG. 6. For one embodiment, the downward facing surface of opaque media 115 may reflect radiation 180, e.g., downward, through opening 152 and onto mirror 155. Mirror 155 reflects the light through filter 160, which filters the infrared radiation from radiation 180 and directs the visible light from radiation 180 through lens 165. Lens 165 focuses the visible light onto sensor 170, which converts the visible light into an image signal containing image data corresponding to one or more images on opaque media 115.

In the transparent scanning mode of FIG. 7, cold cathode lamp 140 is moved away from carriage 130 and toward platen 110. For one embodiment, cold cathode lamp 140 may be aligned with opening 152 in carriage 130 so that cold cathode lamp 140 is directly above opening 152, as shown in FIG. 7. For one embodiment, the transparent media or template 125 containing transparent media 120 is inserted into scanner 600 through an opening 620 so that the transparent media or template 125 containing transparent media 120 is located between cold cathode lamp 140 and carriage 130. Note that in the transparent scanning mode, the transparent media or template 125 containing transparent media 120 underlies cold cathode lamp 140, which underlies platen 110, so that cold cathode lamp 140 is interposed between the transparent media or template 125 containing transparent media 120 and platen 110.

Radiation 180, emitted from cold cathode lamp 140, irradiates the transparent media. Radiation 180 that passes through the irradiated transparent media passes though opening 152 and onto mirror 155, as shown in FIG. 7. For a visible-light scan, filter 160 is positioned in the path for radiation 180, and mirror reflects radiation 180 through filter 160, which filters out the infrared radiation from radiation 180 and directs visible light through lens 165. Lens 165 focuses the visible light onto sensor 170, which converts the visible light into an image signal containing image data corresponding to one or more images on the transparent media and any unwanted artifacts that may be present on the transparent media. For an infrared-radiation scan, focus shifter 190 is positioned in the path for radiation 180, and mirror reflects radiation 180 through focus shifter 190, which shifts the focal point of the infrared component and the visible light components so that the infrared component is focused onto sensor 170 after passing through lens 165 and the visible light components are out of focus when they arrive at sensor 170 and are thus prevented from being sensed by sensor 170. Sensor 170 converts the infrared component into an artifact signal containing data corresponding to any unwanted artifacts on the transparent media.

For one embodiment, platen 110 may be located at a different distance from carriage 130 in the transparent scanning mode than in the opaque scanning mode. In the opaque scanning mode, platen 110 is positioned to give an appropriate optical distance between opaque media 115 and the optical components (mirror 155, filter 160, and lens 165) disposed on the bottom of carriage 130. In the transparent scanning mode, platen 110 is positioned to make room for cold cathode lamp 140. For one embodiment, platen 110 may be positioned by moving an upper portion of scanner 100 relative to a lower portion of scanner 100 (or vice versa) before or concurrently with moving cold cathode lamp 140 from its opaque-scanning position in FIG. 6 to its transparent-scanning position in FIG. 7.

Figure 8A:
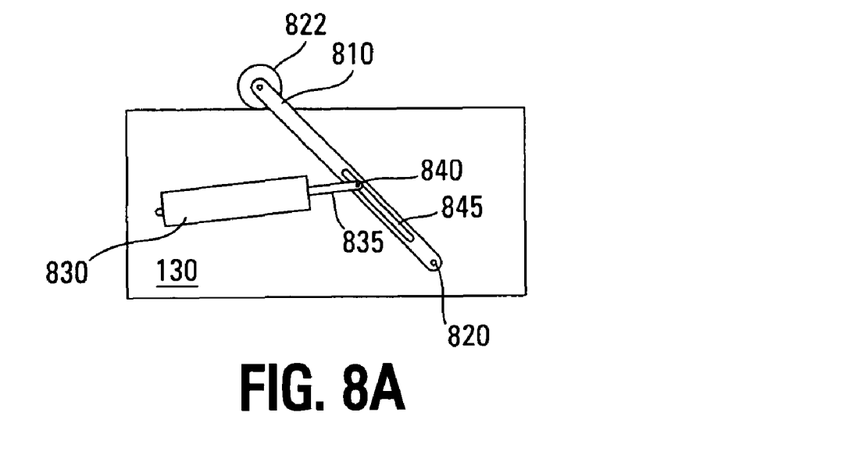
FIGS. 8A and 8B are side views of an embodiment of a carriage of a scanner in two different operating modes, according to another embodiment of the disclosure.
Figure 8B:
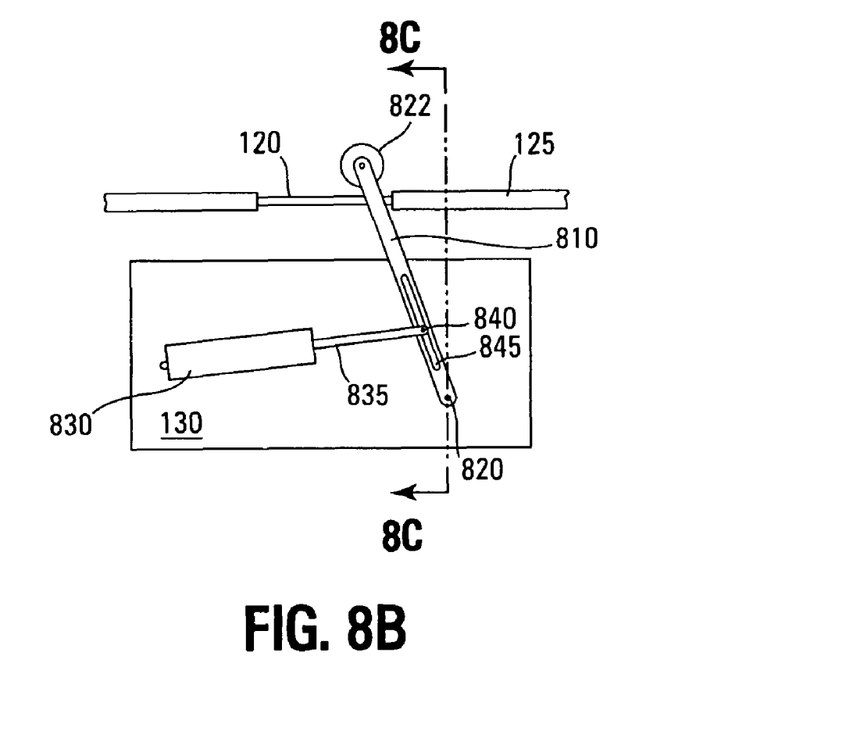
Figure 8C:
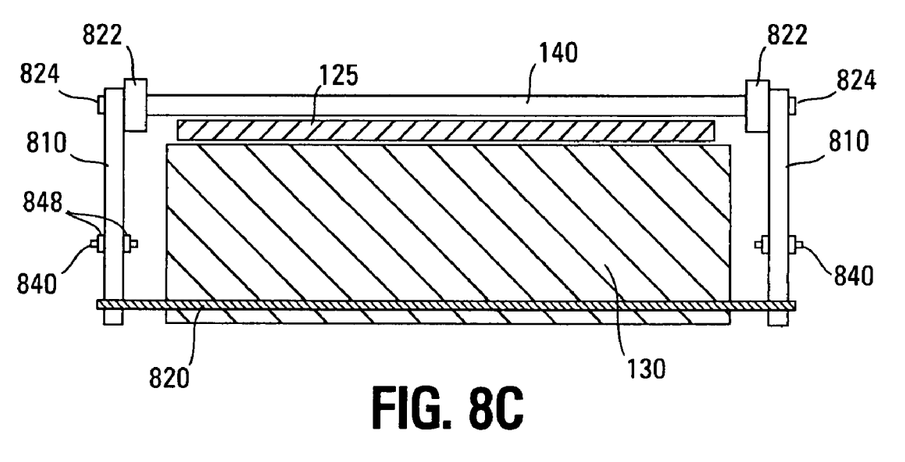
FIG. 8C is a view taken along line 8C-8C of FIG. 8B, according to another embodiment of the disclosure.

FIGS. 8A and 8B are side views of carriage 130, according to another embodiment. FIG. 8C is a view taken along line 8C-8C of FIG. 8B. For one embodiment, arms 810 are pivotally connected to carriage 130 by a shaft 820 that passes through and protrudes from carriage 130 (FIG. 8C). Alternatively, arms 810 may be pivotally connected to pins protruding from carriage 130. For one embodiment, shaft 820 or the pins are fixedly connected to carriage 130, and arms 810 are rotatably connected to their respective pins or shaft 820. For other embodiments, shaft 820 or the pins are rotatably connected to carriage 130, and arms 810 are fixedly attached to their respective pins or shaft 820.

Note that FIG. 8A corresponds to the opaque scanning mode and FIGS. 8B and 8C correspond to the transparent scanning mode. As seen in FIG. 8C, arms 810 straddle template 125, and cold cathode lamp 140 is connected between arms 810 so that cold cathode lamp 140 spans the entire width of template 125 in a direction perpendicular the scanning direction and a direction of motion of arms 810. For one embodiment, cold cathode lamp 140 is mechanically connected to connectors 822, which in turn are mechanically connected to arms 810, e.g., by pins 824, as shown in FIG. 8C. For another embodiment, connectors 822 may also be electrically connected to cold cathode lamp 140 for supplying power to cold cathode lamp 140 from a power source (not shown) of scanner 600 electrically coupled to connectors 822.

For one embodiment, one or both of arms 810 may be respectively connected to a ram 835 of an actuator 830, such as a solenoid, that may be attached to carriage 130, as shown in FIGS. 8A and 8B for one of arms 810. More specifically, a ram 835 may be slidably connected to a respective arm 810 by a pin 840 that passes through a slot 845 in the respective arm 810, as shown in FIGS. 8A and 8B. For one embodiment, a ram 835 may be formed with a pair of tines 848 on an end thereof that straddle an arm 810, as shown in FIG. 8C, and pin 840 passes through tines 848 and slot 845.

For one embodiment, actuator 830 extends or retracts ram 835 in response to electrical signals from a controller (not shown) of scanner 600. As ram 835 extends or retracts, pin 840 slides in slot 845, and arm 810 pivots cold cathode lamp 140 between the position of FIG. 8A, corresponding to the opaque scanning mode, and the position of FIG. 8B, corresponding to the transparent scanning mode. For another embodiment, the controller controls actuator 830 in response to user inputs to computer 105. For example, the controller may send an electrical signal that causes actuator 830 to move cold cathode lamp 140 to the position of FIG. 8B in response to the user selecting the transparency mode of operation, e.g., from a menu displayed on the monitor of computer 105 or from a graphical user interface (not shown) of scanner 600.

For embodiments where shaft 820 is rotatably connected to carriage 130 and arms 810 are fixedly attached to shaft 820, a motor, such as a stepper motor, may be connected to shaft

820. Upon activation, the motor rotates shaft 820, which in turn causes arm 810 to pivot cold cathode lamp 140 between the position of FIG. 8A and the position of FIG. 8B. For one embodiment, the motor may be activated by electronic signals that may be supplied to the motor, e.g., from the controller, as described above in conjunction with actuator 830. For another embodiment, at least one of arms 810 may engage limit switches (not shown) on carriage 130 to stop the motor when the arm 810 is respectively at the positions of FIGS. 8A and 8B.

CONCLUSION

Although specific embodiments have been illustrated and described herein it is manifestly intended that the scope of the claimed subject matter be limited only by the following claims and equivalents thereof.

What is claimed is:

1. A method of operating a scanner, comprising:
   generating visible and infrared radiation from phosphors within a cold cathode lamp;
   irradiating at least partially transparent media with the visible and infrared radiation from the cold cathode lamp;
   sensing infrared radiation that passes through the at least partially transparent media; and
   generating an artifact signal from the sensed infrared radiation, wherein the artifact signal corresponds to one or more unwanted artifacts on the at least partially transparent media.

2. The method of claim 1, wherein an intensity of the infrared radiation is about the same as an intensity of the visible radiation.

3. The method of claim 1 further comprises:
   sensing the visible radiation that passes through the at least partially transparent media; and
   generating an image signal from the sensed visible radiation.

4. The method of claim 3 further comprises preventing the infrared radiation from being sensed while sensing the visible radiation.

5. The method of claim 1 further comprises preventing the visible radiation from being sensed while sensing the infrared radiation.

6. The method of claim 1 further comprises shifting a focal point of the infrared radiation prior to sensing the infrared radiation.

7. The method of claim 1 further comprises positioning the at least partially transparent media overlying a platen of the scanner prior to irradiating at least partially transparent media.

8. The method of claim 1 further comprises positioning the at least partially transparent media between the cold cathode lamp and a carriage of the scanner prior to irradiating at least partially transparent media, wherein the cold cathode lamp, the at least partially transparent media, and the carriage each underlie a platen of the scanner.

9. The method of claim 1, wherein the transparent media is disposed in a template.

10. A method of operating a scanner, comprising:
    concurrently generating visible and infrared radiation from a cold cathode lamp;
    concurrently irradiating at least partially transparent media with the visible and infrared radiation from the cold cathode lamp;
    sensing visible radiation that passes through the at least partially transparent media while preventing the infrared radiation from being sensed;
    generating an image signal from the sensed visible radiation, wherein the image signal corresponds to one or more images on the at least partially transparent media;
    sensing infrared radiation that passes through the at least partially transparent media while preventing the visible radiation from being sensed; and
    generating an artifact signal from the sensed infrared radiation, wherein the artifact signal corresponds to one or more unwanted artifacts on the at least partially transparent media.

11. The method of claim 10, wherein preventing the visible radiation from being sensed comprises shifting a focal point of the visible radiation.

12. The method of claim 10, wherein preventing the infrared radiation from being sensed comprises filtering out the infrared radiation.

13. A scanner, comprising:
    a cold cathode lamp configured to concurrently emit visible and infrared radiation for scanning at least partially transparent media;
    a sensor for sensing visible radiation from the cold cathode lamp that passes through the at least partially transparent media to produce an image signal corresponding to one or more images on the at least partially transparent media and for sensing infrared radiation from the cold cathode lamp that passes through the at least partially transparent media to produce an artifact signal corresponding to one or more unwanted artifacts on the at least partially transparent media; and
    a selector for selectively directing the visible or infrared radiation from the cold cathode lamp that passes through the at least partially transparent media to the sensor.

14. The scanner of claim 13, wherein the cold cathode lamp contains phosphores so that the visible and infrared radiation emitted from the cold cathode lamp have about the same intensities.

15. The scanner of claim 13, wherein the selector comprises a filter for filtering out the infrared radiation from the cold cathode lamp that passes through the at least partially transparent media.

16. The scanner of claim 15, wherein the selector further comprises a focus shifter for focusing the infrared radiation from the cold cathode lamp that passes through the at least partially transparent media onto the sensor and for defocusing the visible radiation from the cold cathode lamp that passes through the at least partially transparent media from the sensor.

17. The scanner of claim 16, wherein the selector further comprises an actuator for selectively actuating the filter or the focus shifter into a path for the visible and radiation from the at least partially transparent media.

18. The scanner of claim 13, wherein the cold cathode lamp is selectively movable between a first position for scanning the at least partially transparent media and a second position for scanning substantially opaque media.

19. The scanner of claim 18 further comprises a movable carriage, wherein the cold cathode lamp is connected to the movable carriage for movement therewith.

20. The scanner of claim 19, wherein the sensor and selector are disposed on the movable carriage.

21. The scanner of claim 20 further comprises a clear platen overlying the movable carriage and the cold cathode lamp.

22. The scanner of claim 13 further comprises:
a clear platen for receiving the at least partially transparent media or substantially opaque media for scanning;
a first movable carriage overlying the platen, wherein the cold cathode lamp is connected to the first movable carriage for movement therewith, wherein the cold cathode lamp overlies the platen;
a second movable carriage underlying the platen, wherein the sensor and selector are disposed on the second carriage; and
a light source connected to the second carriage for movement therewith, wherein the light source connected to the second carriage underlies the platen, wherein the light source connected to the second carriage is for scanning the substantially opaque media.

23. The scanner of claim 22, wherein the first and second carriages move concurrently for scanning the at least partially transparent media.

24. The scanner of claim 22 further comprises a cover that selectively overlies the platen, wherein the second carriage and the cold cathode lamp are disposed in the cover.

25. The scanner of claim 22 further comprises an adaptor that is removably locatable on the platen during a scan of the at least partially transparent media, wherein the second carriage and the cold cathode lamp are disposed in the adaptor.

* * * * *